United States Patent [19]

Lange et al.

[11] Patent Number: 5,152,986

[45] Date of Patent: Oct. 6, 1992

[54] PREPARATION AND USE OF ION EXCHANGE RESINS LOADED WITH QUINOLONECARBOXYLIC ACID DERIVATIVES

[75] Inventors: Peter M. Lange, Leverkusen; Alfred Mitschker, Odenthal; Arundev H. Naik; Hubert Rast, both of Leverkusen; Martin Scheer, Wuppertal; Herbert Voege, Leverkusen, all of Fed. Rep. of Germany

[73] Assignee: Bayer Aktiengesellschaft, Leverkusen, Fed. Rep. of Germany

[21] Appl. No.: 426,123

[22] Filed: Oct. 24, 1989

Related U.S. Application Data

[63] Continuation-in-part of Ser. No. 203,354, Jun. 6, 1988, abandoned.

[30] Foreign Application Priority Data

Jun. 13, 1987 [DE] Fed. Rep. of Germany ....... 3719764

[51] Int. Cl.⁵ .................. A61K 31/74; A61K 31/505

[52] U.S. Cl. ............... 424/78.14; 424/78.15; 424/442

[58] Field of Search .......... 424/442, 79, 78.14, 424/78.15

[56] References Cited

U.S. PATENT DOCUMENTS

| | | | |
|---|---|---|---|
| 3,051,623 | 8/1962 | Hays et al. | 424/79 |
| 3,317,388 | 5/1967 | Shetty et al. | 424/79 |
| 4,762,709 | 8/1988 | Sheumaker | 424/79 |
| 4,826,982 | 5/1989 | Masuzawa et al. | 546/363 |
| 4,871,832 | 10/1989 | Nayakawa et al. | 544/363 |
| 4,874,764 | 10/1989 | Ueda et al. | 544/363 |
| 4,980,353 | 12/1990 | Grohe et al. | 544/363 |

Primary Examiner—Thurman K. Page
Assistant Examiner—Peter F. Kulkosky
Attorney, Agent, or Firm—Sprung Horn Kramer & Woods

[57] ABSTRACT

Known antibacterial quinolonecarboxylic acid derivatives such as ciprofloxacin are administered to animals in their food in the form of weak cation exchangers loaded therewith. The taste is much improved and the animals accept the material more readily.

11 Claims, No Drawings

PREPARATION AND USE OF ION EXCHANGE RESINS LOADED WITH QUINOLONECARBOXYLIC ACID DERIVATIVES

This application is a continuation-in-part of application Ser. No. 203,354, filed Jun. 6, 1988, now abandoned.

The present invention relates to ion exchange resins which are loaded with quinolonecarboxylic acid derivatives, processes for their preparation and their use.

It has long been known to bind pharmaceutically active compounds to ion exchange resins in order, for example, to make active compounds having a pronounced inherent odor more utilizable (Swiss Patent Specification 383,552). It is also known to bind pharmaceutically active compounds to ion exchange resins in order to effect uniform release of the active compound over a longer period of time (EP-OS (European Published Specification) 42,818).

It is furthermore known to bind anthelmintic active compounds to ion exchange resins in order to influence the flavor of the active compounds (DE-OS (German Published Specification) 3,028,082).

Quinolonecarboxylic acids, and their derivatives, bound to ion exchange resins as described hereinbelow were hitherto unknown.

The present invention relates to:

1. Weak cation exchange resins which are loaded with quinolonecarboxylic acid derivatives of the formula (I)

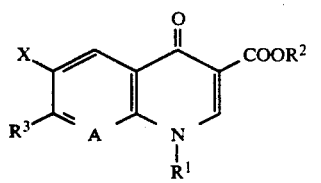

in which

R$^1$ represents methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl or 2,4-difluorophenyl, R$^2$ represents hydrogen, alkyl having 1 to 4 carbon atoms or (5-methyl-2-oxo-1,3-dioxol-4-yl)-methyl, R$^3$ represents methyl or a cyclic amino group such as

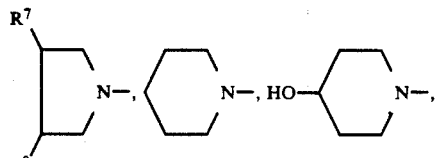

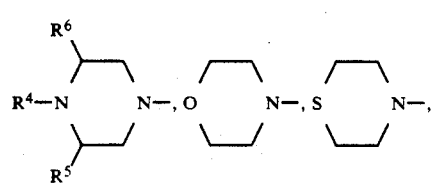

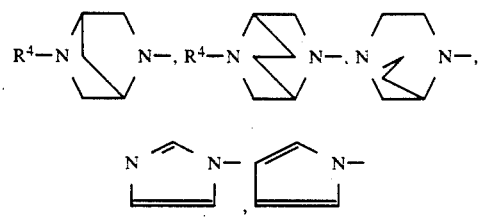

wherein

R$^4$ represents hydrogen, alkyl having 1 to 4 carbon atoms, 2-hydroxyethyl, allyl, propargyl, 2-oxopropyl, 3-oxobutyl, phenacyl, formyl, CFCl$_2$-SO, CFCl$_2$-SO$_2$-, CH$_3$O-CO-S-, benzyl, 4-aminobenzyl or the radical

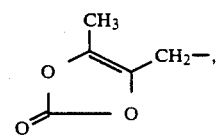

R$^5$ represents hydrogen or methyl,

R$^6$ represents hydrogen, alkyl having 1 to 4 carbon atoms, phenyl or benzyloxymethyl, R$^7$ represents hydrogen, amino, methylamino, ethylamino, aminomethyl, methylaminomethyl, ethylaminomethyl, dimethylaminomethyl, hydroxyl or hydroxymethyl, R$^8$ represents hydrogen, methyl, ethyl or chlorine, X represents fluorine, chlorine or nitro and A represents N or C-R$^9$, wherein R$^9$ represents hydrogen, halogen such as fluorine or chlorine, methyl or nitro or alternatively, together with R$^1$, can form a bridge of the structure

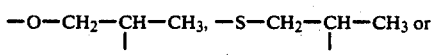

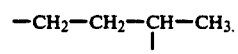

2. Process for the preparation of ion exchange resins which are loaded with quinolonecarboxylic acid derivatives of the formula (I) by treating ion exchange resins with solutions or suspensions of quinolonecarboxylic acid derivatives of the formula (I) in water or in polar solvents.

3. Use of ion exchange resins which are loaded with quinolonecarboxylic acid derivatives of the formula (I), to improve the flavor and also to delay the release of the quinolonecarboxylic acid derivatives of the formula (I), 4. Medicaments, including feed medicaments, which contain ion exchange resins which are loaded with quinolonecarboxylic acid derivatives of the formula (I).

5. Solid, orally administered medicaments and also feedstuffs which contain ion exchangers which are loaded with quinolonecarboxylic acid derivatives of the formula (I).

Suitable weak cation exchange resins can have a matrix which is gelatinous or macroporous. Possible base monomers for the ion exchange polymerizable monomers which can be converted into cation exchanger resins by suitable functionalization. Monomers which may be mentioned are, for example, (meth)acrylates, (meth)acrylonitrile and also styrene derivatives. Polyvinyl compounds, such as, for example, divinylbenzene, ethylene glycol dimethacrylate or methylene bisacrylamide are employed as further comonomers for the preparation of the base polymers. Condensation resins, which lead to cation exchangers, such as, for example, the resins resulting from the reaction of phenol and formaldehyde with polyamines, are also suitable as carriers for the quinolonecarboxylic acid derivatives of the formula (I).

The utilizable ion exchangers are not new. The preparation of these resins is described, for example, in Ullmanns Enzyklopadie der techn. Chemie (Ullmann's Encyclopaedia of Industrial Chemistry) Vol. 13, 4th edition, pages 279 to 307, especially pages 299 to 305 and particularly page 301. The preferred macroporous resins can exhibit variable pore volumes. The degree of cross-linking of the suitable ion exchange resins should preferably be up to 20% and particularly preferably up to 121%. The synthetic resins are present in particle sizes from 50 to 1300 μm, preferably from 100 to 300 μm.

The use of ground ion exchangers may be mentioned in particular. In this case, the grinding can occur before or after the loading with the quinolonecarboxylic acids of the formula (I).

Particularly suitable as the weak cation exchange resin are carboxyl containing resins, especially such as those identified as Lewatit CNP, viz. Lewatit CNP/80, CNP/80-BG, CNP/80-ST, CNP/80-WS and CNP LF.

Such resins are particularly suited since they bind the active compound of the animal medication strongly enough to mask its bitter taste, i.e. dissociation in the mouth and on the tongue of the animal is low enough to mask the bitter taste. Otherwise the animal would not take up enough medicament. However, once the salt formed by the cation exchanger and the active compound has passed the taste region and comes down the gut into the digestive tract it has to dissociate. Good dissociation in the digestive tract is essential in order to ensure blood levels of the active compound high enough to be effective. These demands are in conflict with each other. These demands are also different from the classical slow release formulations for which ion-exchange salts have been used hitherto and wherein the only condition the slow release formulation has to fulfill is that the active material is freed over a period of time.

It has been shown, and is exemplified hereinbelow, that strong cation exchange resins form salts which do not dissociate in water and therefore will not taste bad. However, the strong resinous salts do not free enough active amount in the digestive tract. Surprisingly, salts of weak cation exchangers do not dissociate in water, and therefore also do not taste bad. However, in contrast to the other salts, in the digestive tract they set free their load of active compound, thus guaranteeing sufficient blood levels.

The quinolonecarboxylic acids of the formula (I) and their preparation have been disclosed (DE-OS (German Published Specification) 3,033,157).

Preferred active compounds are quinolonecarboxylic acids of the formula (II)

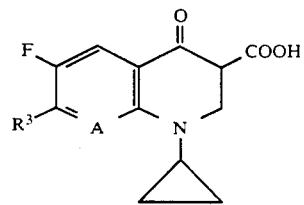

in which
$R^3$ represents

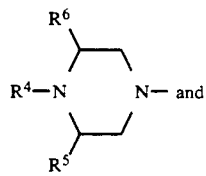

$A$, $R^4$, $R^5$ and $R^6$ have the abovementioned meaning.

Particularly preferred active compounds are quinolonecarboxylic acids of the formula (II), in which $R^3$ represents

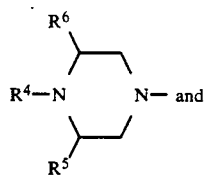

$R^4$ represents hydrogen, methyl or ethyl,
$R^5$ represents hydrogen or methyl, especially hydrogen,
$R^6$ represents hydrogen or methyl, especially hydrogen, and
$A$ has the abovementioned meaning.

The following quinolonecarboxylic acids and their derivatives may be mentioned in particular as active compounds: 1-Cyclopropyl-6-fluoro-1,4-dihydro-4-oxo-7-(1-piperazinyl or 4-methyl- or 4-ethyl-1-piperazinyl)-quinolone-3-carboxylic acid, 1-ethyl-6-fluoro-1,4-dihydro-4-oxo-7-(4-methyl-1-piperazinyl)-quinolone-3-carboxylic acid, 1-ethyl-6-fluoro-1,4-dihydro-4-oxo-7-(1-piperazinyl)-quinolone-3-carboxylic acid, 1-ethyl-6-fluoro-1,4-dihydro-4-oxo-7-(1-piperazinyl)-1,8-naphthyridine-3-carboxylic acid, 9-fluoro-3-methyl-10-(4-methyl-1-piperazinyl)-7-oxo-2,3-dihydro-7,4-pyrido[1,2,4-de]1,4-benzoxazine-6-carboxylic acid,. and also the methyl and ethyl esters of these compounds. Ciprofloxacin and enrofloxacin may be mentioned as being especially preferred.

The degree of loading of the ion exchange resins with the quinolonecarboxylic acid derivatives is between 10 and 150% by weight of the dried ion exchanger, depending on the type of resin.

Release experiments show that the active compound is particularly well released in liquids with pH's from 1 to 3.

The preparation of the ion exchange resins which are loaded with quinolonecarboxylic acid derivatives of the formula (I) takes place in water or polar organic solvents, such as, for example, alcohols such as methanol or ethanol, ketones such as acetone or mixtures thereof.

Water is particularly preferred. Ion exchanger and active compound are in this case stirred in water at room temperature (for example 5 to 24 hours) until the active compound is completely bound.

As already mentioned, the ion exchangers loaded with quinolonecarboxylic acid derivatives of the formula (I) can be used for the preparation of medicaments. As such, medicaments for animals may be mentioned in particular.

Medicament preparations suitable for animals are, for example, those in which improvement of flavor plays a role in intake or in which a delayed release of active compound after administration is sought.

These are, for example, solid preparations such as powders, premixes or concentrates, granules, pellets, tablets, boli and capsules; or suspensions which are administered orally or cutaneously, for example. They are prepared by suspending the resin loaded with active compound in an excipient liquid, where appropriate with the addition of further auxiliaries such as wetting agents, colorants, absorption promotors, preservatives, antioxidants and light screens.

By adding substances which increase the viscosity, these suspensions can also be administered as so-called "semi-solid" preparations such as, for example, ointments. In particular, formulations of this type are employed for the treatment of udder disorders (mastitis) or as oral pastes for cats, dogs and horses.

For the preparation of solid preparations, the resin loaded with active compound is mixed with suitable excipients, where appropriate with the addition of auxiliaries, and brought into the desired form.

Excipients which may be mentioned are all physiologically acceptable solid inert substances. Inorganic and organic substances serve as such. Inorganic substances are, for example, common salt, carbonates such as calcium carbonate, hydrogen carbonates, aluminum oxides, silicas, aluminas, precipitated or colloidal silicon dioxide and phosphates.

Organic substances are, for example, sugar, cellulose, food-stuffs and feedstuffs such as powdered milk, animal meals, ground cereal meals and crushed cereal meals and starches.

Auxiliaries are preservatives, antioxidants and colorants, which have already been mentioned above.

Further suitable auxiliaries are lubricants and glidants, such as, for example, magnesium stearate, stearic acid, talc, bentonites, disintegration-promoting substances such as starch or cross-linked polyvinylpyrrolidone, binding agents, such as, for example, starch, gelatin or linear polyvinylpyrrolidone and also dry binding agents such as microcrystalline cellulose.

For the preparation of suspensions, the resins loaded with active compound are distributed as homogeneously as possible in an excipient medium, where appropriate with the assistance of other auxiliaries such as wetting agents, preservatives or viscosity-increasing substances.

Excipient liquids which may be mentioned are all homogeneous solvents and solvent mixtures, but in particular water.

Wetting agents (dispersing agents) which may be mentioned are:

1. anion-active surfactants including emulsifiers such as Na lauryl sulphate, fatty alcohol ether sulphates, mono/dialkyl polyglycol ether orthophosphate monoethanolamine salt, ligninsulphonates or dioctyl sulphosuccinate,
2. cation-active surfactants, including emulsifiers, such as cetyltrimethylammonium chloride,
3. ampholytic surfactants, including emulsifiers, such as di-Na N-lauryl-$\beta$-iminodipropionate or lecithin,
4. non-ionogenic surfactants, including emulsifiers, such as polyoxyethylated castor oil, polyoxyethylated sorbitan monooleate, sorbitan monostearate, ethyl alcohol, glycerol monostearate, polyoxyethylene stearate, alkylphenol polyglycol ethers and Pluronic ®.

The non-ionic surfactants are particularly preferred.

Further auxiliaries are, for example: Colorants, i.e. all colorants permitted for administration to animals, which can be dissolved or suspended.

Antioxidants such as, for example, sulphites or metabisulphites, such as potassium metabisulphite, ascorbic acid, butylhydroxytoluene, butylhydroxyanisole and tocopherol.

Thickeners or viscosity-increasing substances such as, for example, inorganic thickeners such as bentonites, colloidal silica and aluminum monostearate, organic thickeners such as cellulose derivatives, polyvinyl alcohols and their copolymers, acrylates and methacrylates, alginates, gelatin, polyvinyl pyrrolidone, polyethylene glycols, waxes, gum arabic and xanthan gum or mixtures of the abovementioned substances.

The ion exchange resins loaded with active compound can be added to the feed as such or in the form of premixes or feed concentrates.

Premixes and feed concentrates are mixtures of the active compound with a suitable excipient.

The single feedstuffs or mixtures thereof, and also the abovementioned inert excipients, count as excipients.

Moreover, they can contain further auxiliaries, such as, for example, substances which regulate the flow capability and miscibility, such as, for example, silicas, bentonites and ligninsulphonates. Moreover, antioxidants such as BHT or preservatives such as sorbic acid or calcium propionate can be added. In addition, for powder-binding, liquids such as paraffin oils, vegetable oils and propylene glycols can be admixed to the premixes.

The resins loaded with active compound can be present in the formulations alone or mixed with other active compounds, mineral salts, trace elements, vitamins, proteins, colorants, fats or flavorings.

Other active compounds can be, for example, penicillins, their salts and derivatives, such as, for example, the procaine salt of penicillin G, or derivatives thereof such as oxacillin or cloxacillin.

The administration of the ion exchange resins loaded with active compound preferably takes place together with the feed.

Single feedstuffs of vegetable origin such as hay, beets, cereals, cereal by-products, single feedstuffs of animal origin such as meat, fats, milk products, bonemeal, fish products, and furthermore single feedstuffs such as vitamins, proteins, amino acids, for example DL-methionine, salts such as calcium carbonate and common salt count as feed. Supplementary feedstuffs, finished feedstuffs and mixed feedstuffs also count as feed. These containing single feedstuffs in a composition which guarantees balanced nutrition with respect to the energy and protein supply and also the supply of vitamins, mineral salts and trace elements.

The concentration of the ion exchangers in the feed is normally about 0.01–500 ppm, preferably 10–200 pm.

PREPARATION EXAMPLES

Example 1

100 ml of a suspension of 5 g of enrofloxacin in demineralized water are stirred with 35 ml of Lewatit φ S 100 H+ form until the clearing of the aqueous phase. This process was then repeated until no clear aqueous phase can be obtained, even after stirring for 24 hours. After separation of the resin, the amount of enrofloxacin taken up is determined by differential weighing of the dried resin before and after loading. 7.7 g of enrofloxacin are bound in this experiment.

Example 2

2714 ml of Lewatit ® SPC 108 H+-form are stirred overnight together with 5000 ml of demineralized water and 782 g of enrofloxacin. The resin is isolated from the clear aqueous phase and washed twice with one bed volume of water each time. After drying for 48 hours at 60° C. in a vacuum drying cabinet, 1496 g of the preparation according to the invention are thus obtained.

EXAMPLE 3

80 ml of Lewatit ® CNP H+-form are stirred at room temperature together with 500 ml of demineralized water and 8 g of enrofloxacin. After stirring for 3 hours, the aqueous phase is clear. The ion exchanger has bound the entire active compound.

FORMULATION EXAMPLES

4 Premix For Feed Medicaments

| | |
|---|---|
| Enrofloxacin-ion exchanger according to Example 2 (4.85 g correspond to 2.5 g of enrofloxacin) | 4.85 kg |
| Wheat flour | 95.15 kg |
| | 100.00 kg |

Preparation

The substances are homogeneously mixed in a mixer.

5. Enrofloxacin-Ion Exchanger According To Example 2

| | |
|---|---|
| (9.7 g correspond to 5.0 g of enrofloxacin) | 9.7 kg |
| vegetable oil | 4.0 kg |
| limestone meal | 86.3 kg |
| | 100.0 kg |

The lime meal is premixed with the vegetable oil and the active compound resin is homogeneously distributed therein.

6. Composition Of An Oral Paste (For Example For Dogs And Cats)

| | |
|---|---|
| Enrofloxacin-ion exchanger according to Example 2 (1.88 g correspond to 1 g of enrofloxacin) particle size - mean value 0.1 mm | 1.88 kg |
| glycerol | 10.00 g |
| benzyl alcohol | 1.00 g |
| flavoring | 0.20 g |
| Methylhydroxypropyl cellulose gel 2% to 100 ml | |

Preparation

A 2% strength methylhydroxypropyl cellulose gel is prepared in a customary manner. Benzyl alcohol and flavoring are dissolved and the active compound according to the invention is suspended therein.

7. Composition For a Granulate

| | |
|---|---|
| 1. Enrofloxacin-ion exchanger according to Example 2 (18.8 g correspond to 10.0 g of enrofloxacin) | 18.8 g |
| 2. Lactose | 50.0 g |
| 3. Corn starch | 29.2 g |
| 4. Gelatin | 2.0 g |
| | 100.0 g |

The substances 1, 2 and 3 are mixed. A gelatin solution is prepared from 4 using 22.0 g of water. The mixture is kneaded with it. The solid dough is comminuted through a grater and dried and then sieved to the desired particle size.

8. Composition

| | |
|---|---|
| Enrofloxacin-ion exchanger according to Example 2 | 12.5 kg |
| Limestone meal | 86.0 kg |
| Polyoxyethylated castor oil | 1.5 kg |
| | 100.0 kg |

Limestone meal is mixed together with polyoxyethylated castor oil until homogeneous. The active compound is then added and mixed to homogenity.

USE EXAMPLES

A. Determination Of The Active Compound Concentration In The Blood Serum Of Pigs Which Received The Ion Exchanger Loaded With Active Compound Administered With The Feed.

Piglets having a mean weight of 14.8 kg each received twice daily 0.3 kg of feed for rearing piglets which was mixed with the indicated amount of enrofloxacin. In each case, blood was taken 1 hour after feeding and the content of active compound in the serum determined. The following values were established:

| Content of active compound ppm | Level of active compound µg/ml | |
|---|---|---|
| | 1 hr. after 1st feeding | 1 hr. after 2nd feeding |
| 100 | 0.3 | 0.5 |
| 200 | 0.6 | 0.6 |
| 400 | 1.1 | 1.0 |

B. Determination Of The Acceptance Of Medicated Feed By Pigs

Piglets with a mean weight of 14.8 kg received, twice daily, 0.3 kg of feed for rearing piglets to which was added the pure active compound enrofloxacin, and ion exchange resin which was loaded with active compound. The residual feed in the trough was determined after the given times. The following results were established in this way:

| Content of active compound ppm | Number of animals | Residual feed in % after | | |
|---|---|---|---|---|
| | | 15 | 30 | 60 min |
| 0 | 9 | 5 | 0 | 0 |
| 400 (pure active compound) | 12 | 80 | 70 | 70 |
| 400 (active compound bound to ion exchanger) | 11 | 10 | 0 | 0 |

C. Simulated Taste Trials Based On Binding And Release

The following ion exchangers loaded with Enrofloxacin were prepared:
1. Ion exchanger with —$SO_3^-H^+$ binding groups: 2714 ml of Lewatit ® SPC 108 H+form were stirred overnight together with 5000 ml of demineralized water and 782 g of Enrofloxacin. The resin was isolated from the clear aqueous phase and washed twice with one bed volume of water each time. After drying for 48 hours at 60° C. in a vacuum drying cabinet, 1496 g of the preparation were obtained. The dry ion exchanger has a 38% content of Enrofloxacin.
2. Ion exchanger with —COO$^-$H$^+$ binding groups: 80 ml of Lewatit ® CNP H+-form were stirred at 60° C. together with 500 ml of demineralized water and 8 g of Enrofloxacin. After stirring for 3 hours, the aqueous phase was clear. The ion exchanger bound all the active compound. The dry ion exchanger had a 30.5% content of Enrofloxacin.

Samples of the loaded ion-exchangers prepared according to these 1 and 2 were used in the following trials:

A Trial simulating taste (From former experiments it is known that in order to avoid refusal of an edible formulation containing Enrofloxacin by pigs due to the bitter taste of the formulations the content of free Enrofloxacin has to be below 10 ppm.)

A1 2.63 g of the loaded ion exchanger of 1 was stirred at room temperature in 1 liter of demineralized water. After 1 hour the water overlay was analyzed and a content of <10 ppm Enrofloxacin was found.

A2 3.27 g of the loaded ion exchanger of 2 was stirred at room temperature in 1 liter of demineralized water. After 1 hour the water overlay was analyzed and a content of <10 ppm Enrofloxacin has been determined.

The results show that both ion-exchange resins bind Enrofloxacin sufficiently strongly to avoid bad taste in edible formulations.

B1 2.63 g of the loaded ion exchanger of 1 was stirred at room temperature in 1 liter of 0.1N HCl. After 72 hours only 20–30% of the Enrofloxacin was freed.

B2 3.27 g of the loaded ion exchanger of 2 was stirred at room temperature in 1 liter of 0.1N HCl. After 24 hours 100% of the bound Enrofloxacin was freed.

This shows that only the weak cation-exchange resin freed the active compound sufficiently to enable its therapeutic use.

It will be appreciated that the instant specification and claims are set forth by way of illustration and not limitation, and that various modifications and changes may be made without departing from the spirit and scope of the present invention.

What is claimed is:

1. A weak carboxyl-containing cation exchange resin loaded to the extent of about 10 to 150% of its dry weight with a quinolonecarboxylic acid derivative of the formula $$\text{(I)}$$

in which
  $R^1$ represents methyl, ethyl, propyl, isopropyl, cyclopropyl or phenyl;
  $R^2$ represents hydrogen, alkyl having 1 to 4 carbon atoms or (5-methyl-2-oxo-1,3-dioxol-4-yl)-methyl,
  $R^3$ represents a cyclic amino group of the formula $$R^4-N\begin{pmatrix}R^6\\ \\R^5\end{pmatrix}N-,\ R^4-N\begin{pmatrix}\\ \\ \end{pmatrix}N-\text{ or } R^4-N\begin{pmatrix}\\ \\R^5\end{pmatrix}N-,$$

wherein
  $R^4$ represents hydrogen, alkyl having 1 to 4 carbon atoms, 2-hydroxyethyl, allyl, propargyl, 2-oxopropyl, 3-oxobutyl, phenacyl, formyl, $CFCl_2$-S-, $CFCl_2$-$SO_2$-, $CH_3O$-CO-S-, benzyl, 4-aminobenzyl or a radical of the formula $R^5$ represents hydrogen or methyl,
  $R^6$ represents hydrogen, alkyl having 1 to 4 carbon atoms, phenyl or benzyloxymethyl,
  X represents fluorine, chlorine or nitro and
  A represents N or C-$R^9$, wherein
    $R^9$ represents hydrogen, halogen, methyl or nitro or also, together with $R^1$, can form a bridge of the structure $$-O-CH_2-\underset{|}{CH}-CH_3, -S-CH_2-\underset{|}{CH}-CH_3 \text{ or}$$

$$-CH_2-CH_2-\underset{|}{CH}-CH_3.$$

2. A weak cation exchange resin according to claim 1, in which
  $R^3$ represents

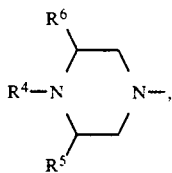

$R^4$ represents hydrogen, methyl or ethyl,
$R^5$ represents hydrogen or methyl, and
$R^6$ represents hydrogen or methyl.

3. A weak cation exchange resin according to claim 2, in which $R^5$ and $R^6$ represent hydrogen.

4. A weak cation exchange resin according to claim 1, in which the quinolone-carboxylic acid derivative is ciprofloxacin.

5. A weak cation exchange resin according to claim 1, in which the quinolone-carboxylic acid derivative is enrofloxacin.

6. An animal feed comprising an edible material and a loaded weak cation exchange resin according to claim 1.

7. In the administration to an animal of a quinolone-carboxylic acid derivative of the formula

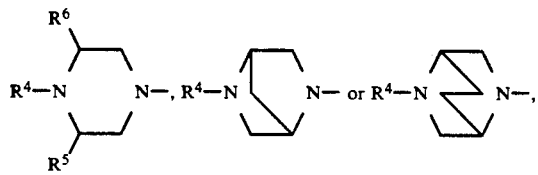

in which
$R^1$ represents methyl, ethyl, propyl, isopropyl, cyclopropyl or phenyl;
$R^2$ represents hydrogen, alkyl having 1 to 4 carbon atoms or (5-methyl-2-oxo-1,3-dioxol-4-yl)-methyl,
$R^3$ represents a cyclic amino group of the formula

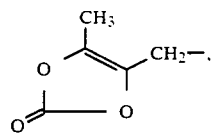

wherein
$R^4$ represents hydrogen, alkyl having 1 to 4 carbon atoms, 2-hydroxyethyl, allyl, propargyl, 2-oxopropyl, 3-oxobutyl, phenacyl, formyl, $CFCl_2$-S-, $CFCl_2$-$SO_2$-, $CH_3O$-CO-S-, benzyl, 4-aminobenzyl or a radical of the formula

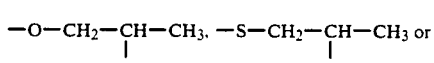

$R^5$ represents hydrogen or methyl,
$R^6$ represents hydrogen, alkyl having 1 to 4 carbon atoms, phenyl or benzyloxymethyl,
X represents fluorine, chlorine or nitro and
A represents N or C-$R^9$, wherein
$R^9$ represents hydrogen, halogen, methyl or nitro or also, together with $R^1$, can form a bridge of the structure

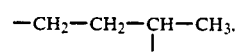

the improvement which comprises administering such derivative loaded to the extent of about 10 to 150% of its dry weight onto a weak carboxylic-containing cation exchange resin and admixed with the animal's feed.

8. The method according to claim 7, in which $R^3$ represents

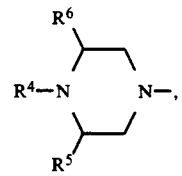

$R^4$ represents hydrogen, methyl or ethyl,
$R^5$ represents hydrogen or methyl, and
$R^6$ represents hydrogen or methyl.

9. The method according to claim 7, in which $R^5$ and $R^6$ represent hydrogen.

10. The method according to claim 7, in which the quinolone-carboxylic acid derivative is ciprofloxacin.

11. The method according to claim 7, in which the quinolone-carboxylic acid derivative is enrofloxacin.

* * * * *